United States Patent
McGuckin, Jr. et al.

(10) Patent No.: US 6,764,464 B2
(45) Date of Patent: Jul. 20, 2004

(54) INTRODUCER SHEATH WITH RETAINER

(75) Inventors: James F. McGuckin, Jr., Radnor, PA (US); Paul Tashjian, King of Prussia, PA (US)

(73) Assignee: Rex Medical, L.P., Conshohocken, PA (US)

( * ) Notice: Subject to any disclaimer, the term of this patent is extended or adjusted under 35 U.S.C. 154(b) by 190 days.

(21) Appl. No.: 09/996,437

(22) Filed: Nov. 28, 2001

(65) Prior Publication Data

US 2002/0068899 A1 Jun. 6, 2002

Related U.S. Application Data

(60) Provisional application No. 60/251,567, filed on Dec. 6, 2000.

(51) Int. Cl.$^7$ ............................................. A61M 29/00
(52) U.S. Cl. ...................................... 604/104; 604/108
(58) Field of Search ........................... 604/158, 164.01, 604/164.03, 164.07, 164.1, 165.01, 165.04, 170.03, 171, 264, 523, 536, 104–105, 108–109

(56) References Cited

U.S. PATENT DOCUMENTS

| | | |
|---|---|---|
| 4,043,346 A | 8/1977 | Mobley et al. |
| 4,995,868 A | 2/1991 | Brazier |
| 5,019,039 A | 5/1991 | Anderson |
| 5,273,529 A | 12/1993 | Idowu |
| 5,352,198 A | 10/1994 | Goldenberg et al. |
| 5,437,644 A | 8/1995 | Nobles |
| 5,509,900 A | 4/1996 | Kirkman |
| 5,702,365 A | 12/1997 | King |
| 5,713,870 A | 2/1998 | Yoon |
| 5,716,325 A | 2/1998 | Bonutti |
| 5,769,821 A | 6/1998 | Abrahamson et al. |
| 5,817,062 A * | 10/1998 | Flom et al. ................. 604/174 |
| 5,840,067 A | 11/1998 | Berguer et al. |
| 5,857,999 A | 1/1999 | Quick et al. |
| 5,882,340 A | 3/1999 | Yoon |
| 5,971,960 A * | 10/1999 | Flom et al. ................. 604/174 |
| 5,976,172 A | 11/1999 | Homsma et al. |
| 6,071,263 A | 6/2000 | Kirkman |
| 6,187,000 B1 | 2/2001 | Davison et al. |

FOREIGN PATENT DOCUMENTS

| | | |
|---|---|---|
| DE | 4315135 | * 12/1994 |
| EP | 0589563 | 3/1994 |

* cited by examiner

Primary Examiner—Loan H. Thanh
(74) Attorney, Agent, or Firm—Neil D. Gershon

(57) ABSTRACT

A surgical introducer sheath comprising a first member having a first longitudinally extending lumen dimensioned to receive a surgical instrument therethrough, a second member having a second longitudinally extending lumen dimensioned to receive the first member, and a retainer adjacent a distal portion of the second member movable from a first retracted position to a second extended position to limit proximal movement of the introducer sheath. Rotational movement of the second member in a first direction moves the retainer to the extended position and rotational movement of the second member in a second direction moves the retainer to a retracted position.

20 Claims, 10 Drawing Sheets

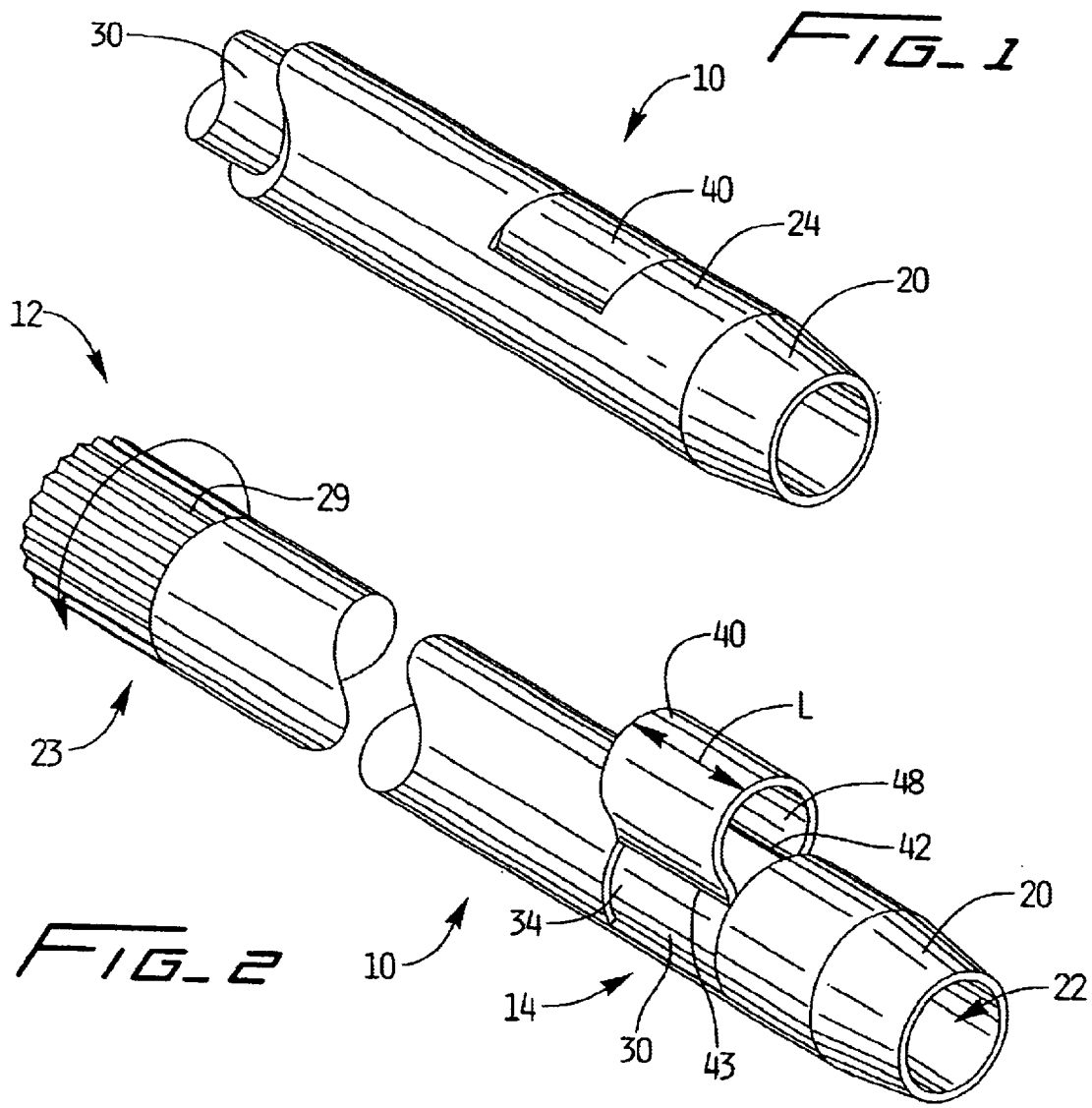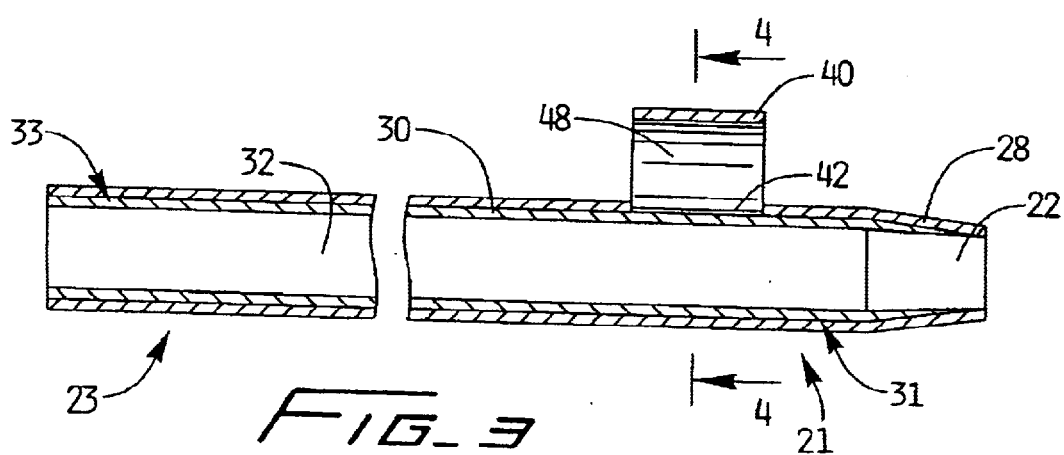

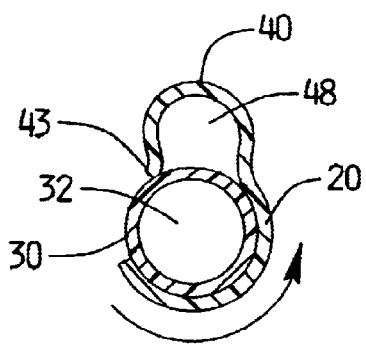
FIG_4
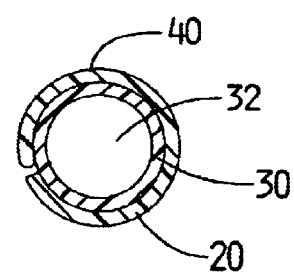
FIG_5
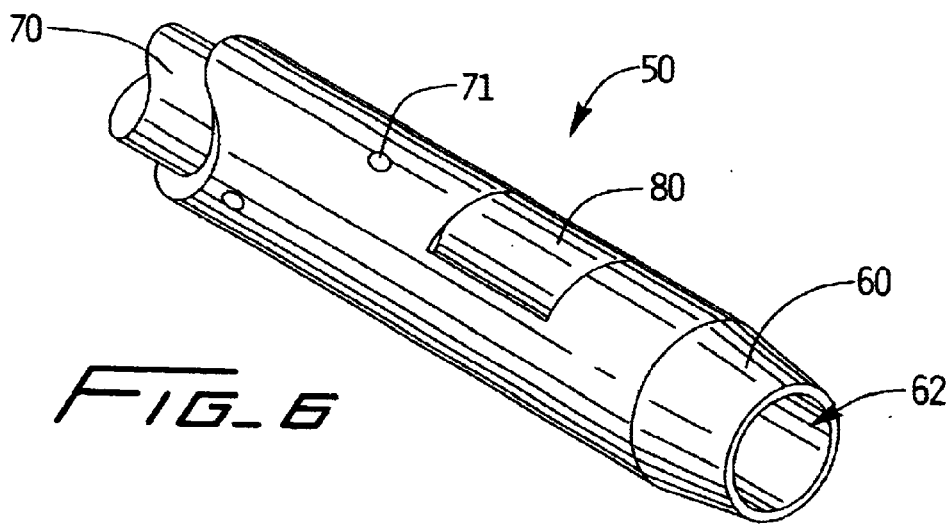
FIG_6
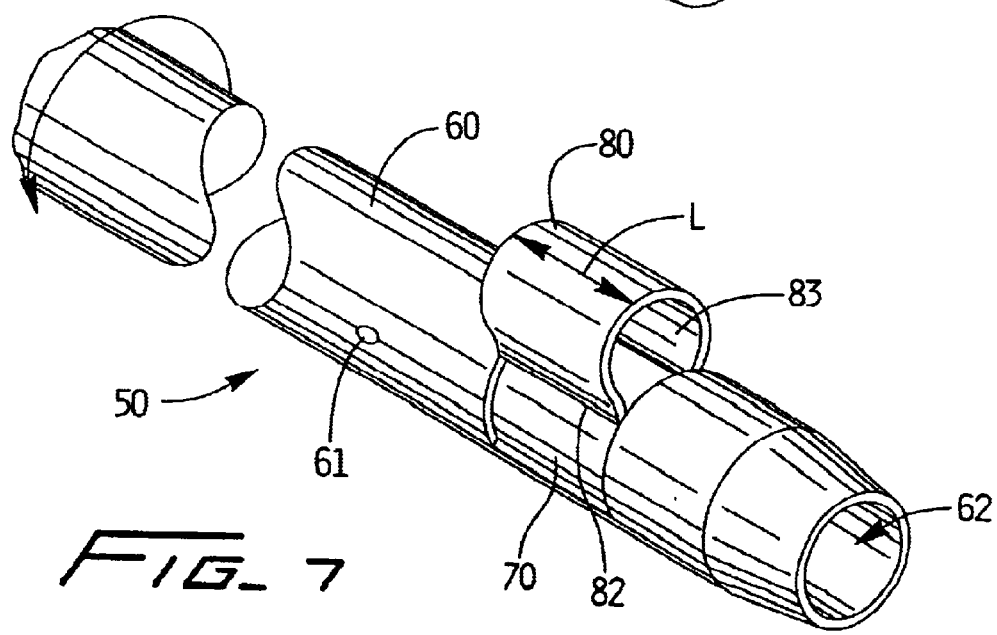
FIG_7

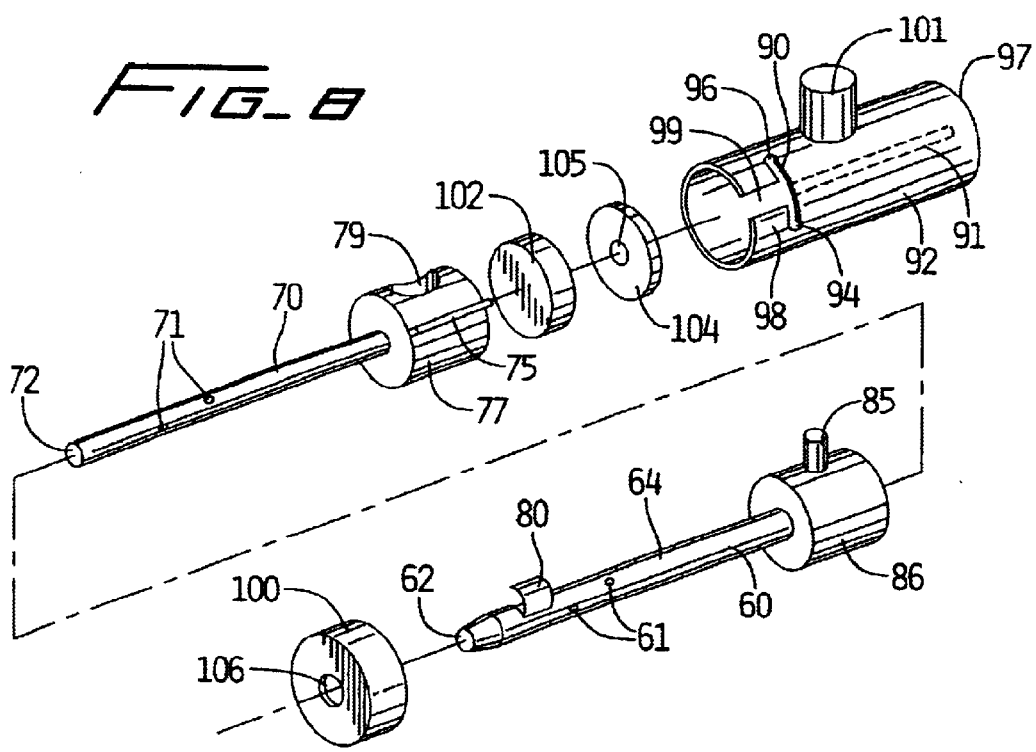
FIG_8
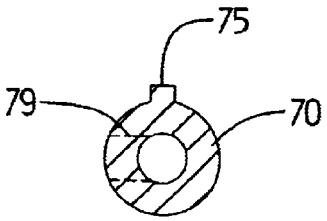
FIG_8A
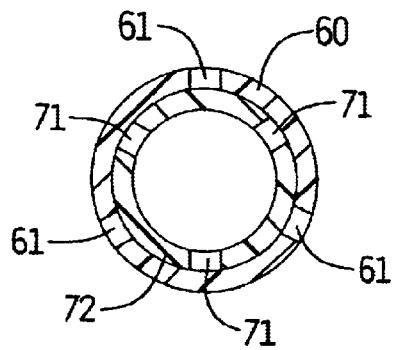
FIG_8B
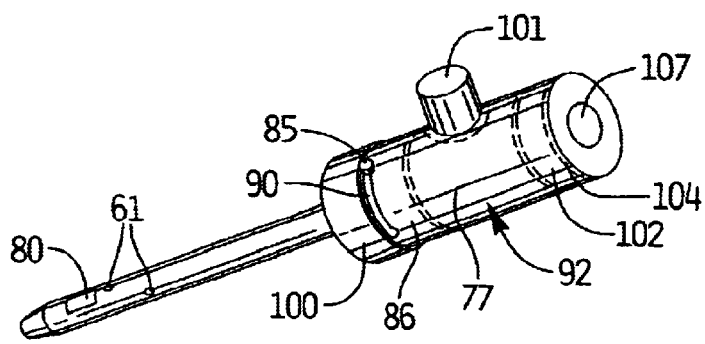
FIG_9

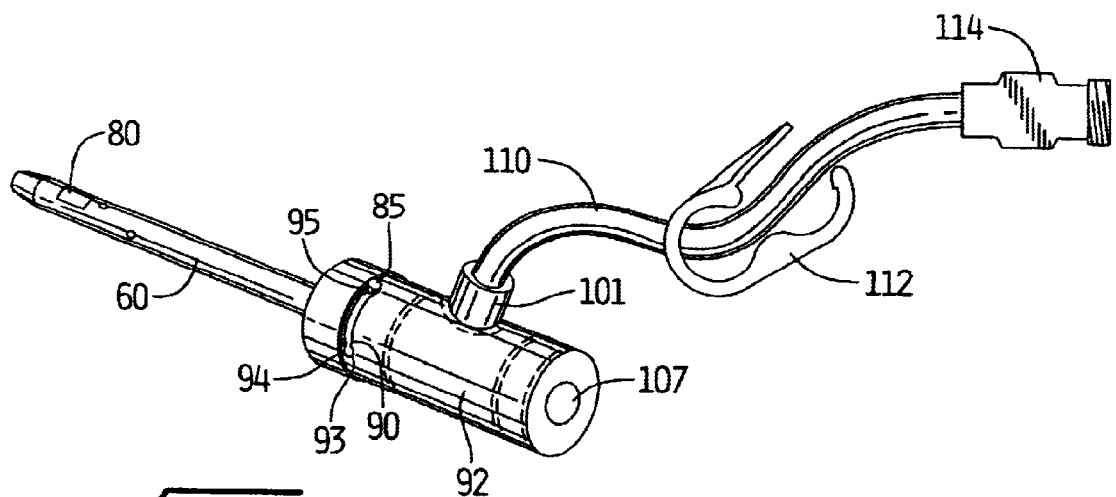
FIG_10
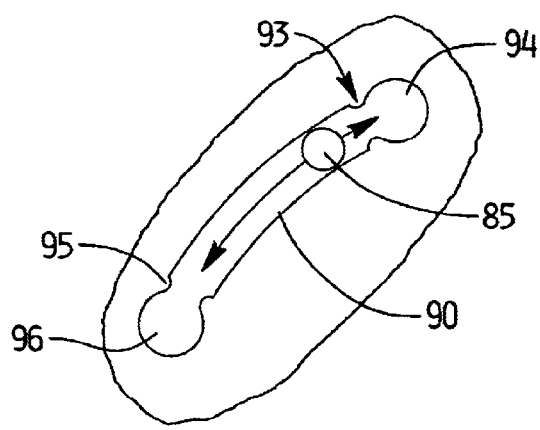
FIG_10A
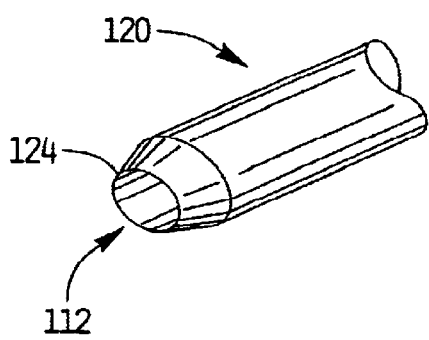
FIG_11
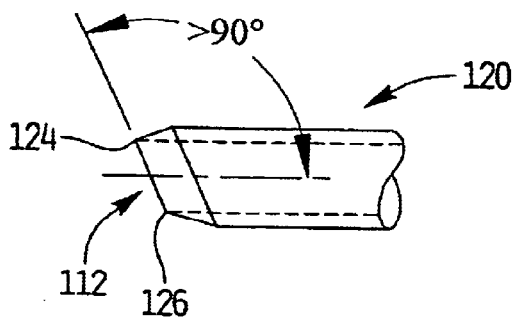
FIG_12

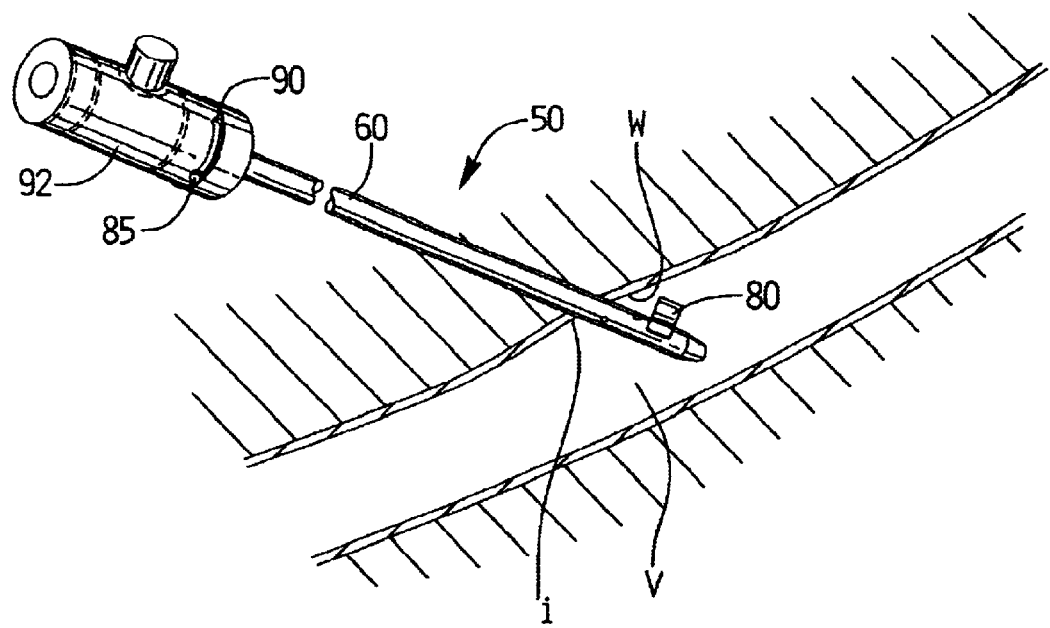
FIG_13
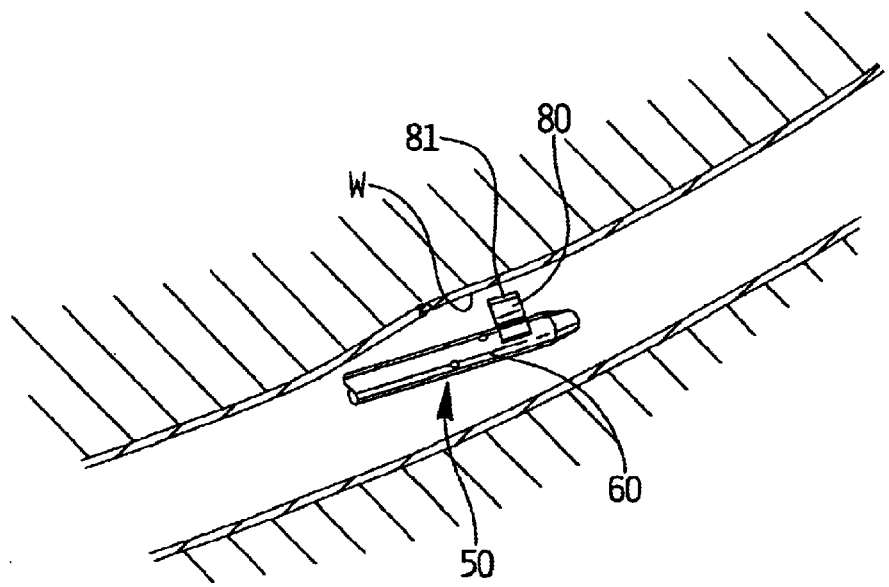
FIG_14

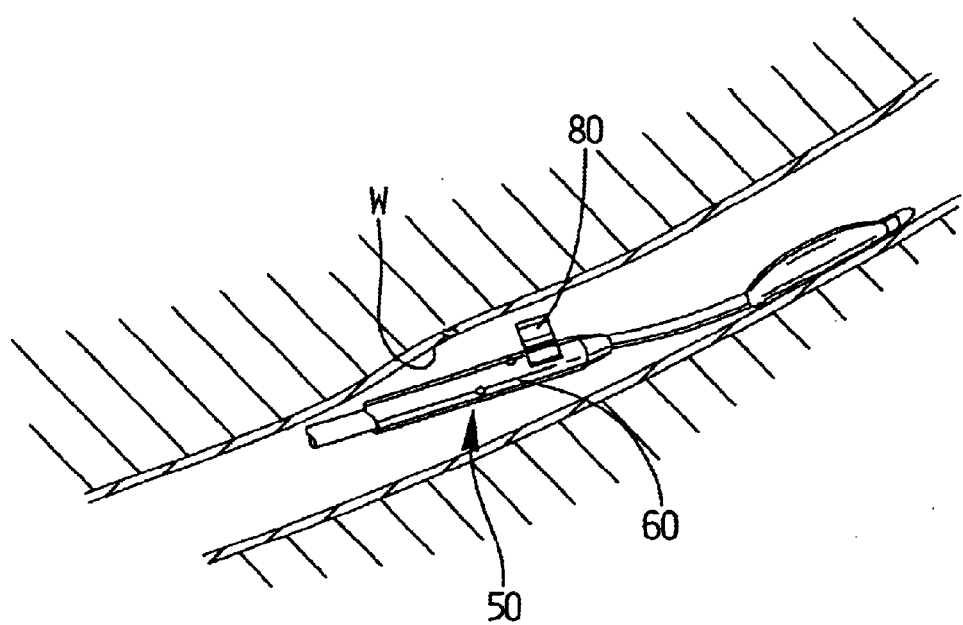
FIG_15
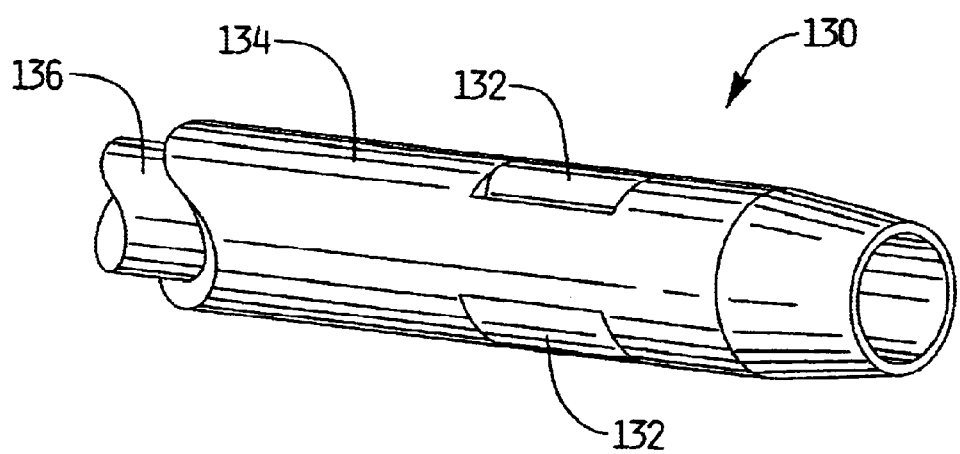
FIG_20

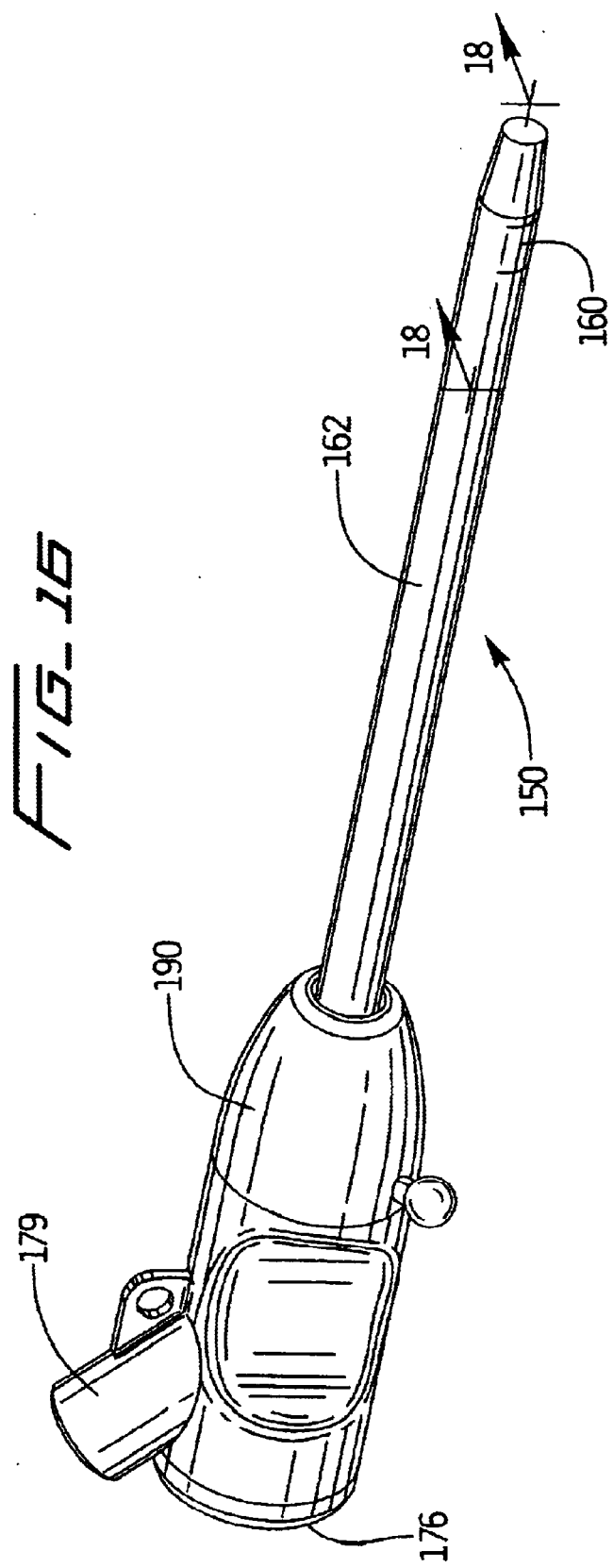

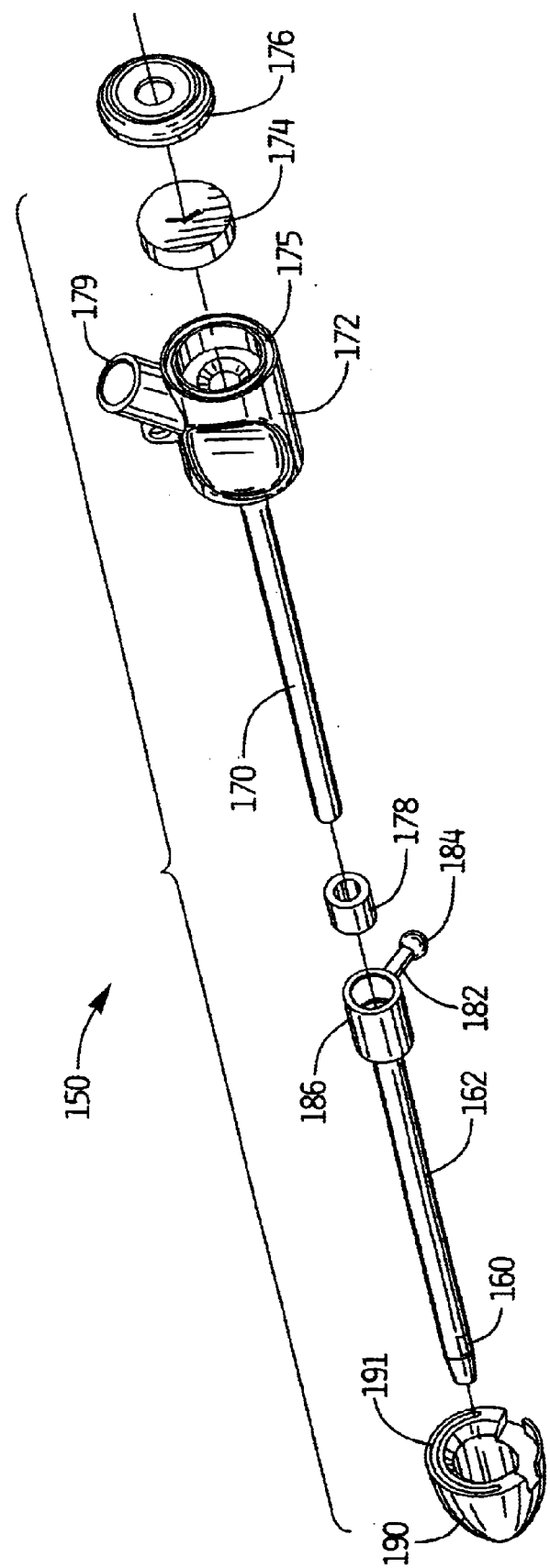

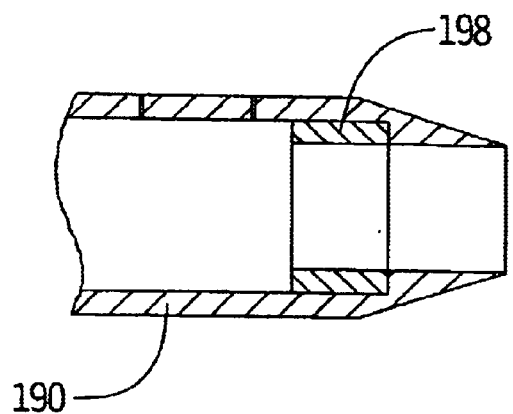
FIG_18
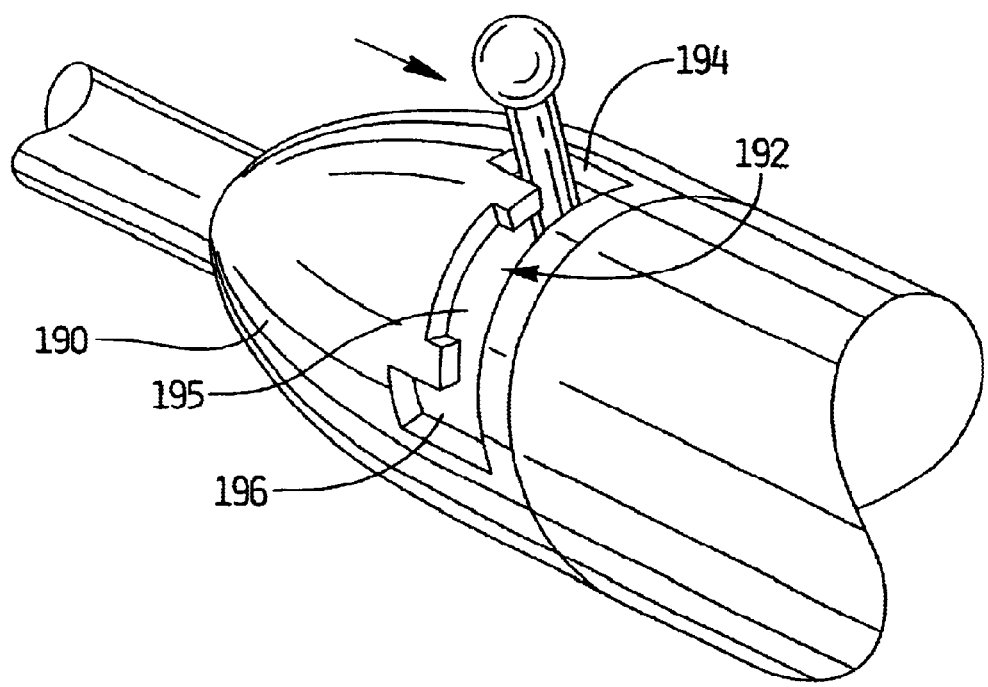
FIG_19

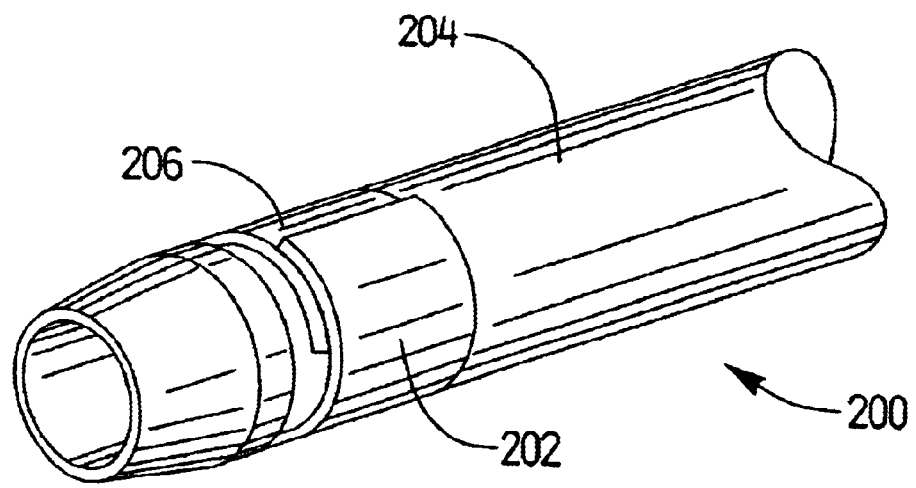
FIG_21
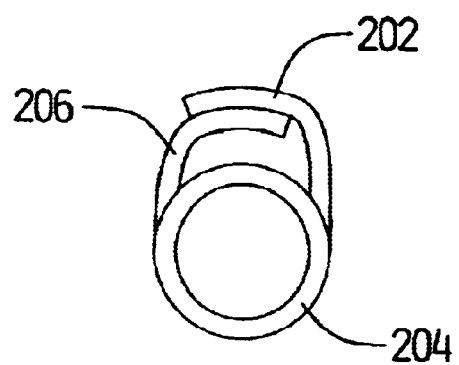
FIG_22

INTRODUCER SHEATH WITH RETAINER

BACKGROUND

This application claims priority from provisional application serial No. 60/251,567, filed Dec. 6, 2000, the entire contents of which are incorporated herein by reference.

TECHNICAL FIELD

This application relates to an introducer sheath and more particularly to a vascular introducer sheath having a retainer to prevent dislodgement during use.

BACKGROUND OF RELATED ART

An introducer sheath is commonly used in vascular surgery as an access port for surgical instruments. The introducer sheath has a central passageway to accommodate such instrumentation and is inserted through a skin incision and into the vessel wall, such as the renal or femoral artery or vein, so the instruments can access the interior of the vessel. The introducer sheath can also be inserted into dialysis grafts to provide access to the graft. The introducer sheaths have peripheral, cardiac, and neurovascular applications.

Once the surgical introducer sheath is placed, various instruments are inserted and withdrawn through the passageway into the vessel interior, depending on the surgical procedure. Examples of such instrumentation include dilators, angioplasty balloon catheters, stent deployment catheters, angiographic instruments, thrombectomy devices and embolization instruments. These instruments typically having an outer diameter close to the internal diameter of the introducer sheath which means they will usually abut the inside wall of the sheath. This relatively tight fit oftentimes results in excessive frictional engagement with the inside wall of the sheath, causing dislodgement of the sheath during instrument withdrawal through the passageway in the sheath. Additionally, surgical instrumentation which include an inflatable balloon, when initially inserted through the sheath have a smaller diameter because the balloon is tightly wrapped around the catheter. However, after the balloon is inflated inside the vessel and then deflated for withdrawal, it is not as tightly wrapped as initial insertion. Thus, when the balloon catheter is withdrawn through the introducer sheath, there is a greater frictional contact with the inside wall of the sheath and therefore a greater likelihood of dislodgement.

Dislodgement of the sheath creates numerous problems. If the position of the sheath is altered by removal of an instrument, when the next instrument is inserted, it will not properly be positioned at the surgical site. Thus the surgeon must undertake the time consuming task of repositioning the sheath and instrument within the vessel. The problems with dislodgement become more acute if withdrawal of the instrument actually pulls the introducer sheath out of the vessel wall incision altogether. This can occur if there is sufficient frictional contact with the instrument and introducer sheath, and a sufficient proximal force is applied by the surgeon. Such undesirable removal of the introducer sheath can cause loss of blood, air aspiration which can result in air embolisms possibly causing stroke, and an increased risk of infection and morbidity. Additionally, since the surgeon needs to reintroduce the introducer sheath into the vessel, the surgeon may be unable to locate the exact prior incision site, thereby having to enlarge the incision site or create a second incision, thereby causing additional blood loss and increasing the difficulty of closing the vessel incision(s) at the end of the procedure. Vessel fatigue can also result because re-introduction of the sheath requires insertion of a needle and dilator through the vessel wall.

Another disadvantage of complete dislodgement of the sheath is the additional time required to re-introduce the sheath. This time loss can be especially significant if re-introduction is required at a critical time of the procedure. That is, if the sheath is fully withdrawn from the vessel, access to the vessel will be temporarily denied, thereby interrupting the surgical procedure which can mean appropriate instrumentation, perhaps even life-saving instrumentation, cannot be inserted to the surgical site.

Due to the concern of dislodgement, surgeons sometimes over-insert the introducer sheath so the tip is spaced further from the incision. This way, if the sheath is inadvertently pulled proximally, it will have some room to move before it is pulled out fully from the incision. However, over-insertion of the introducer sheath can adversely affect surgical access as the surgical site can be blocked by the sheath, especially if the site is adjacent the incision.

Therefore, it would be advantageous to provide a mechanism to retain the introducer sheath within the vessel. However, such mechanism needs to be configured so as not to damage the vessel wall. Consequently, a retaining mechanism must effectively strike a balance between sufficient strength to retain the introducer sheath while providing atraumatic contact with the vessel wall.

The need therefore exists for an atraumatic introducer sheath which has greater retention capabilities, to thereby minimize the chances of dislodgement. By minimizing the likelihood of dislodgement, the foregoing risks to the patient would advantageously be eliminated.

SUMMARY

The present invention overcomes the disadvantages and deficiencies of the prior introducer sheaths by advantageously providing an introducer sheath having a retainer that is selectively extendable with respect to the sheath, thereby functioning to retain the sheath within the vessel. Extending the retainer radially from the sheath creates an enlarged diameter region greater than the diameter of the incision into the vessel to prevent withdrawal of the sheath through the incision, and in smaller vessels, enabling the retainer to frictionally engage the vessel wall to restrict sliding movement of the sheath.

More specifically, the present invention provides a surgical vascular introducer sheath comprising a first member having a first longitudinally extending lumen configured and dimensioned to receive a surgical instrument therethrough, a second member having a second longitudinally extending lumen configured and dimensioned to receive the first member, and a retainer adjacent a distal portion of the second member movable from a first retracted position to a second extended position, in response to movement of the second member, to limit proximal movement of the introducer sheath. Preferably, rotational movement of the second member in a first direction moves the retainer to the extended position and rotational movement in a second direction moves the retainer to the retracted position. The second member is preferably substantially fixed longitudinally during rotation.

Preferably, the retainer comprises a flap having a curved configuration in the extended position and an opening to allow blood flow therethrough. Preferably a first portion of the flap extends from the second member and a second portion of the flap is attached to the first member.

The first and second members may each have a plurality of side holes for blood flow for dialysis wherein the side holes are out of alignment when the retainer is in the retracted position and the side holes are moved into alignment when the second member is rotated to move the retainer into the extended position.

The introducer sheath may further comprise a locking mechanism for maintaining the retainer in the extended position. The locking mechanism may comprise a locking pin slidable within a locking groove having a narrowed section to retain the pin. Preferably, a proximal portion of the first and second members are positioned within a housing with the locking groove positioned on the housing and the locking pin extending from the second member. The housing may further have an internal keyway slot to receive a key extending from the first member to prevent rotation of the first member. The locking mechanism may alternately comprise a post slidable within a locking groove having a radial region and first and second axial regions.

The present invention also provides a surgical sheath for providing a passageway for instrumentation into a vessel comprising a tubular member having a lumen extending longitudinally therein dimensioned and configured for receiving surgical instruments therethrough and means spaced proximally from the distalmost tip of the tubular member for limiting proximal movement of the sheath with respect to the vessel. The limiting means is movable from a first position to a second position extending laterally with respect to the tubular member and enabling blood flow therethrough in the second position.

The tubular member preferably includes inner and outer tubular members and the limiting means preferably comprises a flap movable to the second position in response to rotational movement of the outer tube. In an alternate embodiment, the limiting means comprises first and second flaps movable to the extended position in response to rotational movement of the outer tubular member.

The present invention also provides a surgical sheath for providing a passageway for instrumentation into a vessel comprising an outer tubular member having a first side hole in a sidewall and an inner tubular member disposed within the outer tubular member and having a passageway for receiving surgical instruments therethrough and having a second hole in a sidewall. A retainer at a distal portion of the outer tubular member is movable from a non-blocking position substantially flush with the outer tubular member to a blocking position extending radially outwardly from the outer tubular member. The first and second side holes are moved into alignment when the retainer is moved to its blocking position.

A method for retaining a surgical introducer sheath is also provided comprising:

- inserting an introducer sheath having inner and outer tubular members and a retainer into body tissue;
- rotating the outer tubular member of the introducer sheath to move the retainer from a retracted position to an extended position so the retainer extends radially outwardly,
- introducing a surgical instrument into the introducer sheath;
- performing a surgical step with the surgical instrument;
- withdrawing the surgical instrument, the retainer limiting proximal movement of the introducer sheath during withdrawal of the surgical instrument; and
- rotating the outer tubular member of the introducer sheath to return the retainer to its retracted position.

BRIEF DESCRIPTION OF THE DRAWINGS

Preferred embodiment(s) of the present disclosure are described herein with reference to the drawings wherein:

FIG. 1 is a perspective view of a first embodiment of the introducer sheath of the present invention with the retainer in the retracted position;

FIG. 2 is a perspective view of the introducer sheath of FIG. 1 with the retainer in the extended position;

FIG. 3 is a longitudinal cross-sectional view of the introducer sheath of FIG. 2 with the retainer in the extended position;

FIG. 4 is a transverse cross-sectional view taken along lines 4—4 of FIG. 3;

FIG. 5 is a transverse cross-sectional view similar to FIG. 4 except showing the retainer in the retracted position;

FIG. 6 is a perspective view of the distal portion of a second embodiment of the introducer sheath of the present invention having side holes for dialysis and showing the retainer in the retracted position;

FIG. 7 is a perspective view of the distal portion of the introducer sheath of FIG. 6 showing the retainer in the extended position;

FIG. 8 is an exploded view of the introducer sheath of FIG. 6;

FIG. 8A is a transverse cross-sectional view showing the orientation of the side port and keyway of the housing;

FIG. 8B is a transverse cross-sectional view showing the dialysis holes of the inner and outer tubular members out of alignment prior to deployment of the retainer;

FIG. 9 is a perspective view of the introducer sheath of FIG. 6 showing the components in phantom inside the housing;

FIG. 10 is a perspective view of the introducer sheath of FIG. 6 showing the tubing extending from the side port for either blood withdrawal or blood return;

FIG. 10A is an enlarged view of the locking pin and groove of FIG. 10;

FIG. 11 is a perspective view of the distal portion of an alternate embodiment of the introducer sheath having an angled tip to facilitate insertion;

FIG. 12 is a side view of the introducer sheath of FIG. 11;

FIG. 13 illustrates the introducer sheath of FIG. 6 inside a vessel with the retainer in the extended position to prevent withdrawal of the introducer sheath through the incision;

FIG. 14 illustrates the distal portion of the introducer sheath of FIG. 6 inserted into a small vessel wherein the retainer, in its extended position, frictionally engages the vessel wall to limit proximal movement of the introducer sheath;

FIG. 15 illustrates a catheter being withdrawn from the introducer sheath of FIG. 6, the retainer engaging the vessel wall to limit proximal movement;

FIG. 16 is a side perspective view of a third embodiment of the introducer sheath of the present invention;

FIG. 17 is an exploded view of the introducer sheath of FIG. 16;

FIG. 18 is a cross-sectional view taken along lines 18—18 of FIG. 16;

FIG. 19 is an enlarged perspective view of a portion of the introducer sheath of FIG. 16 showing the ball lock engaged in the slot; and FIG. 20 is a perspective view of a fourth alternate embodiment of the introducer sheath of the present invention having two retainers;

FIG. 21 is a perspective view of a distal portion of a fifth alternate embodiment of the introducer sheath of the present invention having two overlapping flaps; and FIG. 22 is a front view of the introducer sheath of FIG. 21 showing the overlapping flaps in the extended position.

DETAILED DESCRIPTION OF PREFERRED EMBODIMENTS

Introducer sheaths are commonly used in vascular surgery to provide a passageway for instrumentation. The introducer sheath is inserted into a vessel or a graft (e.g. a dialysis graft) and a variety of instruments for performing the specific surgical procedure are introduced therethrough to access the surgical site. Since the instruments are repeatedly inserted and withdrawn during the surgical procedure, and have a diameter closely matching the internal diameter of the sheath, the introducer sheath has the tendency to be dislodged, and perhaps even withdrawn from the vessel incision as discussed above. Additionally, certain instruments, such as balloon catheters, may have a larger diameter during withdrawal then insertion, thereby increasing the chances of dislodgment. The introducer sheaths of the present invention advantageously have a retainer for limiting proximal movement and preventing full dislodgement of the introducer sheath during surgery. That is, the retainer is extendable from the sheath to create an enlarged diameter or circumferential portion exceeding the size of the vessel incision and in smaller vessels, frictionally engaging the vessel wall.

Referring now in detail to the drawings where like reference numerals identify similar or like components throughout the several views, FIGS. 1–5 illustrate a first embodiment of the introducer sheath of the present invention, designated generally by reference numeral 10.

The introducer sheath 10 has a proximal portion 12, a distal portion 14, an outer tubular member 20 and an inner tubular member 30 disposed concentrically within the outer tubular member 20. A retainer 40, in the form of a curved or U-shaped flap, extends from outer tube 20 and is positioned proximally of the distalmost tip. Retainer 40 is movable from a retracted position where it is substantially flush with the outer surface 24 of outer tube 20 as shown in FIG. 1, to an extended (blocking) position where it extends radially outwardly from the outer tube 20 as shown in FIG. 2. This radial movement increases the overall circumference or diameter of the outer tube 20, thereby causing the sheath 10 to engage the vessel wall or wall surrounding the incision in the manner described below.

Outer tube 20, preferably circular in cross section as shown, (although oval or other shapes can be utilized) has a distal portion 21, a proximal portion 23 and a central longitudinal lumen 22 dimensioned and configured to receive inner tube 30. A cutout in the outer tube 20 forms flap 40, integrally extending therefrom at edge 42 and which is attached at edge 43 to outer surface 34 of inner tube 30. Distal nose 28 of tube 20 is slightly tapered to facilitate insertion through the incision and vessel.

Inner tube 30 is also preferably circular in cross section (although oval or other shapes can be utilized) and has a distal portion 31 and a proximal portion 33. Central lumen 32 extends longitudinally along the entire length of the inner tube 30 and is configured and dimensioned to receive surgical instruments therethrough, as described below.

Retainer or flap 40 is deployed by rotation of outer tube 20. The surgeon grasps the knurled surface 29 of proximal portion 23 and rotates the outer tube 20 in the direction of the arrow. Such rotation causes flap 40 to move to the extended (deployed) position since flap 40 is attached to inner tube 30 (at edge 48) which remains stationary. Flap 40 is preferably curved and U-shaped as shown to form an opening 43 to allow blood flow therethrough and extend longitudinally alongside outer tube 60 ("L"). The smooth shaped surface provides atraumatic contact with the vessel wall.

FIGS. 6–10 illustrate an alternate embodiment of the introducer sheath of the present invention. Introducer sheath, designated generally by reference numeral 50 is similar to introducer sheath 10 of FIG. 1 in that it has an outer tube 60, an inner tube 70 and a flap 80 extending from outer tube 60 and attached at edge 82 to inner tube 70. Inner tube 70 has a longitudinal lumen 72 for passage of surgical instruments and outer tube 60 has a longitudinal lumen 62 to receive inner tube 70. As in the first embodiment, flap 80, in its retracted position is substantially flush with outer tube 60 and in its extended (blocking) position is curved and in a U-shaped configuration to form opening 83 for blood passage. Flap 80 is preferably integrally formed with outer tube 60, positioned proximally of the distalmost tip of the outer tube, and as shown extends longitudinally alongside a portion of the outer tube 60 as represented by letter "L".

Introducer sheath 50 further includes a retainer locking element to maintain the retainer or flap 80 in the extended position. Turning now to FIG. 8, outer tube 60 has a locking pin 85 extending from enlarged head 86 which is received within transverse locking groove 90 of housing 92. As shown in FIGS. 10 and 10A, locking groove 90 is slightly arcuate and has two lobes 94, 96 at opposite ends and adjacent narrowed regions 93, 95. When the retainer is in the retracted position of FIG. 6, locking pin 85 is seated within lobe 96 and is prevented from movement within the groove 90 by narrowed region 95. To move the retainer to the extended position to limit movement of the introducer sheath 50, locking pin 85 is grasped by the user and moved within groove 90. By supplying sufficient force, locking pin 85 is forced through narrowed region 95, slightly stretching the flexible material around the groove. Movement of locking pin 85 rotates the outer tube 60, while the inner tube 70 remains stationary, thereby moving retainer 80 to its extended position. This pin and groove arrangement also keeps outer tube 60 fixed longitudinally during rotation.

To lock the retainer 80 in its extended position, locking pin 85 is forced through narrowed region 93 into lobe 94. After being slightly stretched by passage of locking pin 85, narrowed region 93 returns to its original configuration to block exit of locking pin 85. Thus, locking pin 85 is prevented from sliding within locking groove 90, thereby blocking outer tube 60 from rotation and maintaining retainer 80 in the blocking (extended) position.

When it is desired to move retainer 60 back to its retracted position, locking pin 85 is forced through narrowed regions 93 and 95, by movement in the reverse direction, and returned to lobe 96. During movement of the outer tube 60 in either direction, inner tube 70 remains stationary due to the engagement of key 75 of enlarged head 77 with keyway slot 91 of housing 92, shown in phantom in FIG. 8. Outer tube 60 is prevented from sliding longitudinally by groove 90. As an alternative to the keyway, an adhesive or any energy welding system, e.g. radiofrequency, ultrasonic, etc., can be utilized to keep the inner tube 70 stationary.

Visual indicators could optionally be provided at the lobes to indicate to the user the position of the retainer. For example, an "R" for retracted can be provided adjacent lobe 96 on the housing 92 and an "E" for extended can be provided adjacent lobe 94.

With continued reference to FIG. 8, housing 92 has assembly slot 99 communicating with groove 90 for ease of assembly. That is, for assembly, locking pin 95 is slid through slot 99 into groove 90 and locking cap 100 is placed over distal portion 98 of housing 92 effectively closing slot 99 to lock pin 85 within groove 90. A valve 102 is positioned within housing 92 to prevent outflow of blood through proximal opening 107 of housing 92. If introducer sheath 50 is used for dialysis as explained below, the valve is preferably a silicone valve to accommodate additional pressure from the vacuum for blood withdrawal. A donut like element 104, preferably composed of foam and having central opening 105, is positioned between valve 102 and proximal wall 97 of housing 92. Donut 104 is preferably laced with a lubricant such as silicone to promote lubricity during insertion of surgical instruments and to prevent valve damage due to friction.

Optionally, the introducer sheath can include a plurality of holes for either blood withdrawal or blood return so the introducer sheath can remain in the body for dialysis. As shown in FIG. 8, outer tube has side openings or holes 61 formed through its outer wall 64 and inner tube 70 has side openings or holes 71 formed through outer wall 74. These holes 61, 71, when aligned, allow for passage of blood through lumen 72, out through side aperture 79 in enlarged head portion 77, and exiting through side port 101 in housing 92. Conventional tubing 110, as shown in FIG. 10, is connected to side port 101. Tubing 110 includes conventional tube clamp 112 and luer fitting 114 which do not form part of this invention and are therefore not further described. If used for dialysis, two introducer sheaths 50 would be provided: one sheath 50 for withdrawal of blood from the vessel for passage to the dialysis machine and a second sheath 50 for return of blood from the dialysis machine to the vessel. Alternatively, if used for dialysis, introducer sheath 50 could be used for blood withdrawal or delivery, and another instrument, such as dialysis needle could be used for opposite blood flow. Also, although three holes are shown, it should be appreciated that various spacings and fewer or greater number of holes could be provided for dialysis or for other procedures.

It should be appreciated that it is also contemplated that the sheath need not be provided with any side holes if dialysis or blood flow for other surgical applications is not intended.

FIG. 8B illustrates the interaction of the side holes 61 and 71 of the outer and inner tubes 60, 70 respectively. When the retainer 80 is in the retracted position, holes 61 and 71 are out of alignment as shown, thereby preventing blood flow through central lumen 72. However, when outer tube 60 is rotated to extend retainer 80 to the blocking (extended) position, side holes 61 are rotated into alignment with side holes 71. Thus when outer tube 60 is locked in the rotated position with locking pin 85 retained in lobe 94, holes 61 and 71 are in alignment and blood can pass through these holes into central lumen 72.

Proximal opening 107 in housing 92 allows for passage of a guidewire and surgical instruments, the guidewire and surgical instruments passing through opening 102 in donut 104, and through valve 102 and opening 106 in cap 100 into central lumen 72.

FIGS. 11 and 12 illustrate an alternate embodiment of the introducer sheath having an angled or beveled end to facilitate insertion. Introducer sheath 120, as shown, has a tip 112 at an angle greater than 90 degrees so that edge 124 will penetrate tissue before edge 126, thereby reducing the penetration force. Such angled tip can be provided on any of the foregoing introducer sheaths.

FIGS. 16–19 illustrate a third embodiment of the locking sheath of the present invention, designated generally by reference numeral 150. Locking sheath 150 is similar to the foregoing locking sheaths in that it has a retainer 160 in the form of a U-shaped flap that is movable between a retracted substantially flush position to a radially extended position with respect to the outer tube 162. Locking sheath 150 differs in the locking structure for the retainer 160 and some of the assembly components.

More specifically, and with reference to FIG. 17, inner tube 170 extends integrally from housing 172. Side port 179 for mounting conventional tubing as described above (not shown) is shown angled at about 45 degrees to reduce mechanical hemolysis. Inner tube 170 is preferably composed of a dark material, achieved for example by adding carbon black or other particles or by inks or pigments, to absorb laser wavelengths to create heat to laser weld the retainer 160 to the inner tube 170 (see FIG. 18). Other methods of attachment are also contemplated.

Seated inside housing 172 is slit valve 174 and end cap 176. Slit valve 174 is press fit within a tapered inner surface of housing 172 and end cap 176 is fitted with recess 175 of housing 172. The end cap 176 preferably has a chamfer to direct instruments inserted therethrough towards the center. Gasket 178 is frictionally seated over inner tube 170 to provide a seal between the inner tube 170 and outer tube 162.

Outer tube 162 has a lumen dimensioned to receive the inner tube 170. Retainer (flap) 160, extending from outer tube 162 is welded to inner tube 170. Post 182, terminating in ball 184, extends from enlarged cylindrical base 186 and functions to lock the retainer 160 in the retracted position and in the extended position. More specifically, and with reference to FIG. 17 and FIG. 19, a slot 192 is formed in front cap 190. Front cap 190 is mounted to housing 172 via a U-shaped groove 191 and corresponding tongue arrangement on housing 172. Slot 192 extends radially along the surface of cap 190 and has two axially extending regions 194, 196 at its ends. When post 182 is in region 194, the retainer 160 is in its retracted position. To rotate the outer tube 162 to move the retainer 160 to the extended position, the user pulls post 182 rearwardly (in the direction of the arrow) along first axis region 194, into radial region 195, and moves the post 182 along radial region 195 into second axial region 196 where the outer tube 162 is secured against rotation and the retainer 160 is maintained in the extended position. Note that post 182 in its normal position is seated within the first or second axial regions 194, 196 and needs to be flexed proximally to release it and guide it through radial region 195. Engagement within axial regions 194, 196 provides a tactile feel to the user. The locking sheath 150 operates in the manner described above and illustrated in FIGS. 13–15.

FIG. 20 illustrates an alternate embodiment wherein locking sheath 130 is provided with two retainers 132, spaced apart as shown. Locking sheath 130 is substantially identical to the locking sheath of FIG. 6, in all other respects. Each retainer 132 is attached to inner tube 136 at an edge and is identical to retainer 80 of FIG. 6. The retainers 132 are shown in their retracted position, and are deployed simultaneously to their U-shaped configurations upon rotation of the outer tube 134 as described above with respect to the embodiment of FIGS. 6–10.

FIGS. 21 and 22 illustrate another alternate embodiment of the locking sheath designated by reference numeral 200 (Only the distal portion is shown). Locking sheath 200 has a retainer (flap) 202 extending from the outer tube 204 and a retainer (flap) 206 extending from the inner tube. Retainer 202 is attached, e.g. welded, to retainer 206 so that upon rotation of outer tube 204, retainer 202 and retainer 206 are moved to the deployed position. The overlapping retainers 202, 206 increase the material strength of the flap.

The tips or any regions of any of the foregoing introducer sheaths can have radiopaque markers to provide visual indication of the sheath tip location. The markers can take a variety of forms such as a circular marker band wrapped around the outer tube or a radiopaque material attached (e.g. welded) or otherwise applied onto the tip or along other regions of the sheath. FIG. 18 shows a marker band 198 formed in the distal tip, composed by way of example, from black tungsten and placed during formation of the tapered tip.

The introducer sheath of the present invention can be made of various dimensions. In a preferred embodiment, the sheath is about 6 French or about 7 French in outer diameter and has a wall thickness of about 0.014 inches (the inner and outer sheath each having a wall thickness of about 0.007 inches).

The interior of the inner tubes of any of the foregoing embodiments can have a hydrophilic coating to facilitate instrument insertion through its lumen by reducing frictional contact. The outer surface of the outer tube could also be provided with a hydrophilic coating to reduce frictional contact with the skin and vessel during insertion. To help keep thrombus from forming on the device, an anti-thrombolytic coating can also be provided.

FIGS. 13–15 illustrate the introducer sheath of the present invention in use. The introducer sheath 50 of FIGS. 6–10 is illustrated and described (with the tubing removed for clarity), it being understood however, that any of the afore-described introducer sheaths would be utilized in a similar manner.

FIG. 13 illustrates introducer sheath 50 positioned inside a vessel "v", such as a common femoral artery. Sheath 50 is inserted through incision "i" in the vessel wall to gain access to the interior of the vessel. Once positioned as shown, the outer tube 60 is rotated to deploy retainer 80 to an extended position as shown. In this extended position, the sheath 50 cannot fit through the incision "i". Consequently when surgical instruments such as a balloon catheter shown in FIG. 15 are inserted and then withdrawn, the retainer 80 will contact the vessel wall around the incision, preventing undesirable withdrawal of the introducer sheath 50 through the incision. Being retained or "locked" inside the vessel, various instruments can be inserted and withdrawn through the sheath lumen 62 without the introducer sheath 50 becoming dislodged and causing the problems associated with such dislodgement discussed above. The pin and groove locking arrangement maintains the retainer 80 in the extended (blocking) position as desired.

When the introducer sheath 50 is ready to be removed from the vessel "v", the outer tube 60 is rotated in the reverse direction, disengaging the pin and groove locking arrangement, to thereby return the retainer to its retracted position substantially flush with the outer surface of the outer tube 60. Thus, the introducer sheath 50 can be withdrawn through incision "i".

When used in smaller vessels, not only will the retainer 80 prevent full withdrawal from the incision, but it will contact the vessel wall "u" downstream of the incision as shown in FIG. 14. This contact results in frictional engagement with the wall, thereby restricting unwanted longitudinal movement of the introducer sheath 50 during withdrawal of surgical instruments, such as the balloon catheter of FIG. 15. The curved surface 81 of flap 80 provides atraumatic contact with the vessel wall.

The introducer sheaths of the present invention can also be utilized in other minimally invasive catheter procedures, including non-vascular procedures such as genitourinary, biliary, and gastrointestinal procedures which require instrument insertions and withdrawals through introducer sheaths.

While the above description contains many specifics, those specifics should not be construed as limitations on the scope of the disclosure, but merely as exemplifications of preferred embodiments thereof. For example, any of the sheath embodiments can optionally be provided with holes for dialysis. Also, if blood flow therethrough is not required, the retainers need not be provided with an opening for blood flow. Although the introducer sheath is preferably composed of Pebax material, other materials such as urethane, nylon, polyethyelene, or polypropylene, or composites with braided components, can be utilized. The sheaths could also be slightly curved or bendable/shapeable. Those skilled in the art will envision many other possible variations within the scope and spirit of the disclosure as defined by the claims appended hereto.

What is claimed is:

1. A surgical vascular introducer sheath comprising:
    a first member having a first longitudinally extending lumen configured and dimensioned to receive a surgical vascular instrument therethrough;
    a second member having a second longitudinally extending lumen configured and dimensioned to receive the first member;
    an infusion side port in fluid communication with an interior lumen of the first member to enable infusion of fluid to assist a vascular procedure; and
    a retainer adjacent a distal portion of the second member, the retainer movable from a first retracted position to a second extended position to limit proximal movement of the introducer sheath, the retainer movable in response to rotational movement of the second member.

2. The introducer sheath of claim 1, wherein rotational movement of the second member in a first direction moves the retainer to the extended position and rotational movement of the second member in a second direction moves the retainer to the retracted position.

3. The introducer sheath of claim 2, wherein the second member is substantially fixed longitudinally during rotation.

4. The introducer sheath of claim 2, wherein the retainer comprises a flap having a substantially curved configuration in the extended position.

5. The introducer sheath of claim 4, wherein the flap includes an opening to allow blood flow therethrough when in the extended position.

6. The introducer sheath of claim 2, wherein a first portion of the retainer extends from the second member and a second portion of the retainer is attached to the first member.

7. The introducer sheath of claim 2, further comprising a locking mechanism for maintaining the retainer in the extended position.

8. The introducer sheath of claim 7, wherein the locking mechanism comprises a locking pin slidable within a locking groove, the groove having a narrowed section to retain the pin.

9. The introducer sheath of claim 1, wherein the infusion port is positioned at an angle to the second tubular member.

10. The introducer sheath of claim 9, wherein the infusion port is positioned at about a 45 degree angle to the second tubular member.

11. The introducer sheath of claim 1, further comprising a seal between the first member and the second member.

12. The surgical sheath of claim 1, wherein the sheath is between about 6 French and about 7 French in outer diameter.

13. A surgical vascular introducer sheath comprising:
a first member having a first longitudinally extending lumen configured and dimensioned to receive a surgical instrument therethrough;
a second member having a second longitudinally extending lumen configured and dimensioned to receive the first member;
a retainer adjacent a distal portion of the second member, the retainer movable from a first retracted position to a second extended position to limit proximal movement of the introducer sheath, the retainer movable in response to movement of the second member;
wherein rotational movement of the second member in a first direction moves the retainer to the extended position and rotational movement of the second member in a second direction moves the retainer to the retracted position, and
a locking mechanism for maintaining the retainer in the extended position, wherein the locking mechanism comprises a post movable within a locking groove, the locking groove configured to lock the retainer in the retracted position by locking the second member against movement in the first direction and the second direction and configured to lock the retainer in the extended position by locking the second member against movement in the first direction and the second direction.

14. The introducer sheath of claim 13, further comprising a housing, wherein a proximal portion of the first and second members are positioned within the housing, the locking groove being positioned on the housing and the post extending from the second member.

15. The introducer sheath of claim 13, wherein the retainer comprises a flap formed integrally with the second member.

16. The introducer sheath of claim 13, wherein the locking groove has a radial region and first and second axial regions.

17. A surgical sheath for providing a passageway for instrumentation into a vessel comprising:
a body including a distalmost tip, an inner tubular member having a lumen extending longitudinally therein configured and dimensioned for receiving surgical instruments therethrough, and an outer tubular member receiving the inner tubular member, the inner tubular member being fixed with respect to the outer tubular member; an infusion side port in fluid communication with an interior lumen of the first member to enable infusion to assist a vascular procedure; and
a retainer spaced proximally from the distalmost tip, the retainer limiting proximal movement of the sheath with respect to the vessel, the retainer being movable by movement of the outer tubular member from a first position to a second position extending laterally with respect to the tubular member and enabling blood flow therethrough in the second position, the retainer including a flag integral with the outer tubular member and attached to the inner tubular member, the flap having an uninterrupted outer surface and being attached to the inner tubular member without additional components forming holes through the flap.

18. The surgical sheath of claim 17, wherein the flap is movable to the second position in response to rotational movement of the outer tube.

19. The surgical sheath of claim 17, further comprising a seal between the inner and outer member.

20. A method for retaining a surgical introducer sheath inside a vessel or vascular graft comprising the steps of:
inserting into a vessel or vascular graft an introducer having inner and outer tubular members and a retainer into body tissue;
rotating the outer tubular member of the introducer sheath to move the retainer out of a first locked position where it is in a retracted position to a second locked position where it is in an extended position so the retainer extends radially outwardly with respect to the introducer sheath, the inner tubular member remaining stationary and the retainer not impeding blood flow;
introducing a surgical vascular instrument into the introducer sheath and into the vessel or vascular graft;
performing a surgical step with the surgical instrument;
withdrawing the surgical instrument, the retainer limiting proximal movement of the introducer sheath during withdrawal of the surgical instrument while allowing distal movement of the introducer sheath; and
rotating the outer tubular member of the introducer sheath to move it from the second locked position to the first locked position to return the retainer to its retracted position.

* * * * *